(12) United States Patent
Mirza et al.

(10) Patent No.: US 7,828,801 B2
(45) Date of Patent: Nov. 9, 2010

(54) EXTERNAL FIXATION DEVICE FOR FRACTURES

(75) Inventors: Ather Mirza, St. James, NY (US); Romi Mirza, Seldon, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 1372 days.

(21) Appl. No.: 10/933,578

(22) Filed: Sep. 3, 2004

(65) Prior Publication Data

US 2006/0064087 A1 Mar. 23, 2006

(51) Int. Cl.
*A61B 17/56* (2006.01)

(52) U.S. Cl. .................................................. 606/54

(58) Field of Classification Search ............ 606/54, 606/55, 57–59, 105, 60
See application file for complete search history.

(56) References Cited

U.S. PATENT DOCUMENTS

| | | | |
|---|---|---|---|
| 1,789,060 A | | 1/1931 | Weisenbach |
| 2,333,033 A | | 10/1943 | Mraz |
| 2,391,537 A | * | 12/1945 | Anderson .................... 606/59 |
| 2,435,850 A | | 2/1948 | Siebrandt |
| 4,135,505 A | | 1/1979 | Day |
| 4,271,832 A | | 6/1981 | Evans et al. |
| 4,299,212 A | | 11/1981 | Goudfrooy |
| 4,488,542 A | | 12/1984 | Helland |
| 4,922,896 A | | 5/1990 | Agee et al. |
| 5,437,666 A | * | 8/1995 | Tepic et al. .................... 606/55 |
| 5,728,096 A | | 3/1998 | Faccioli et al. |
| 5,951,556 A | | 9/1999 | Faccioli et al. |

2004/0133199 A1 * 7/2004 Coati et al. .................... 606/54

OTHER PUBLICATIONS

MacDermid, J.C., "Responsiveness of the disability of the arm, shoulder, and hand (DASH) and patient-rated wrist/ hand evaluation (PRWHE) in evaluating change after hand therapy", J. Hand Ther., vol. 17, pp. 18-23 (2004).

Beaton, D.E., et al., "Measuring the whole or the parts? Validity, reliability, and responsiveness of the Disabilities of the Arm, Shoulder and Hand outcome measure in different regions of the upper extremity", J. Hand Ther., vol. 14 pp. 128-146 (2001) (abstract only).

Muller, M.E., "Classification of fractures-long bones", Berlin: Springer-Verlag, pp. 106-115 (1987).

Flinkkila. T., et al., "Poor interobserver reliability of AO classification of fractures of the distal radius", J Bone Joint Surg [Br], vol. 80-B, pp. 670-672 (1998).

(Continued)

*Primary Examiner*—Eduardo C Robert
*Assistant Examiner*—David Comstock
(74) *Attorney, Agent, or Firm*—Ping Wang; Andrews Kurth, LLP

(57) ABSTRACT

An external fixation device and method, which is designed for the setting and corrective treatment of bone fractures. More particularly, the provision is made for an external orthopaedic wrist fixation device for the setting and corrective treatment of bone fractures which may be encountered in the distal radial portion of the forearm of a patient, through the utilization of novel cross pin arrangements extending through the site of the fracture for fracture fixation and with the absence of the risks and discomfort of encountered Ligamentotaxis.

16 Claims, 13 Drawing Sheets

OTHER PUBLICATIONS

Kreder, H.J., et al., "Consistency of AO fracture classification for the distal radius", J. Bone Joint Surg. [Br], vol. 78, pp. 726-731 (1996).

Cole, R.J., et al., "Radiographic evaluation of osseous displacement following intra-articular fractures of the distal radius: Reliability of plain radiography versus computed tomography", J. Hand Surg., vol. 22, pp. 792-800 (1997).

Kreder, H.J., et al., "X-ray film measurements for healed distal radius fractures", J. Hand Surg., vol. 21, pp. 31-39 (1996).

MacDermid, J.C., et al., "Pain and disability reported in the year following a distal radius fracture: A cohort study", BMC Musculoskeletal Disorders, vol. 4, pp. 1-13 (2003).

Knirk, J.L., et al., "Intra-articular fractures of the distal end of the radius in young adults", J Bone Joint Surg, vol. 68, pp. 647-659 (1986).

McQueen, M., et al., "Colles fracture: does the anatomical result affect the final function?", J Bone Joint Surg, vol. 70-B, pp. 649-651 (1988).

MacDermid, J.C., et al., "Patient rating of wrist pain and disability: a reliable and valid measurement tool", J Orthop Trauma, vol. 12, pp. 577-586 (1998).

MacDermid, J.C., et al., "Responsiveness of the short form-36, disability of the arm, shoulder, and hand questionnaire, patient-rated wrist evaluation, and physical impairment measurements in evaluating recovery after a distal radius fracture", J Hand Surg, vol. 25, pp. 330-340 (2000).

Strauss, E.J., et al., "Evaluation of a novel, nonspanning external fixator for treatment of unstable extra-articular fractures of the distal radius: biomechanical comparison with a volar locking plate", J Trauma, vol. 64, pp. 975-981 (2008).

Fernandez, D.L., et al., "Fractures of the Distal Radius: A practical approach to management (second edition)",Springer-Verlag, pp. 58-60 (2002).

Azegami, S., "Radiological evaluation of distal radius fracture: what junior doctors want to know", Orthogate (2008).

Rogge, R., et al., "An analysis of bone stresses and fixation stability using a finite element model of simulated distal radius fractures", J Hand Surg, vol. 27, pp. 86-92 (2002).

Graham, T.J., "Biochemical aspects of percutaneous pinning for distal redial fractures", Fractures of the distal radius (First Edition), pp. 28-36 (1995).

* cited by examiner

EXTERNAL FIXATION DEVICE FOR FRACTURES

BACKGROUND OF THE INVENTION

1. Field of the Invention

The present invention relates to an external fixation device, which is designed for the setting and corrective treatment of bone fractures. More particularly, the invention is directed to the provision of an external orthopaedic wrist fixation device for the setting and corrective treatment of bone fractures which may be encountered in the distal radial portion of the forearm of a patient, through the utilization of novel cross pin arrangements extending through the site of the fracture for fracture fixation and with the absence of the risks and discomfort of encountered Ligamentotaxis.

Basically, fractures which are encountered in the bones of patients due to various causes are treated and corrected through essentially the selective application of three different generally known methods or concepts. A first one of these concepts or methods is directed to maintaining the fracture site in fixed position through the intermediary of external bandaging, for instance, which may be in the form of plaster casts or similar immobilizing structures encompassing the fracture site.

A second method, which is employed in the setting and correcting of bone fractures by immobilizing the fracture site, resides in the provision of internal fastening devices or splints, which are surgically inserted at the fracture site into the limb of the patient and enclosed therewithin. These internal fastening devices may incorporate rails equipped with screws, rods, nails, pins, wires, or screws per se and plate structures. These devices generally necessitate the implementation of extensive invasive surgical procedures, which may readily lead to infections and are difficult to treat without corrective follow-up surgery, which is required for removing such internal devices subsequent to the healing of the fracture site.

A third method, which is also widely employed in the treatment of fractures, relates to the deployment of an external fixation device or splint having pins mounted thereon, with the pins passing through the skin and soft internal tissues of the patient so as to extend into the bone on opposite sides of a fracture site, and with an external connection member mounting the pins for fixation in their predetermined positions in the bone until healing is completed over a period of weeks or other extended times.

All of these above-mentioned orthopaedic treatment devices and methods are intended to provide for the correction of bone fractures and to propagate healing at an intended minimal degree of discomfort and pain to the patient, while engaged in attempts of minimizing the risks of infection or having to conduct or implement further follow-up surgical procedures which may be deleterious to the health and comfort of the patient.

With regard to the widely employed external fixation devices for the setting and correction of bone fractures that have been proposed and which are currently employed, many diverse types of devices are designed to be utilized in connection with specific kinds of fractures. Although such devices are generally satisfactory in accomplishing their intended purpose, in effect, in effectuating the healing of the fractures, many of these are subject to structural and physical limitations when employed with patients in that they often are quite heavy, and resultingly present a high degree of discomfort to the patient, particularly children or adolescents, during the prolonged periods of use thereof. Alternatively, the devices are of the type which inhibits the mobility at various locations at which the fractures are encountered, such as the knee or the wrist, which may have long lasting or permanent adverse effects on the recovery and regaining of the full use of such limbs or joints.

For instance, a common type of bone fracture which is frequently encountered when patients trip or fall, is a result of the patient trying to regain his or her balance by extending the arms, with the wrists ordinarily taking the major shock or impact during the fall. This leads to open and/or unstable fractures of the distal radius of the forearm, inasmuch as that part of the forearm is subject to the heaviest impact or force when striking against a hard surface or structure.

Heretofore, in the employment of orthopaedic external wrist fixation devices incorporating bone-penetrating pins or wires utilized to immobilize a forearm fracture site while retaining the fractured bone sections in a contacting position, the distal radius portion of the forearm is frequently anchored by pins of the devices to the hand or flexural parts of the wrists, such as the fingers, whereas other pins are anchored to the proximal or downstream site of the forearm fracture. This may cause the hand to be immobilized or limited in its movement, although the pins at the distal or upstream site of the fracture may have their outer ends connected to swivable or movable components of the external fixation device. Nevertheless, this still poses a hindrance to the unencumbered movement of the hand of the patient and may be of a type which does not facilitate an appropriate or rapid healing of the fracture site, and may be a cause of Ligamentotaxis.

Other currently employed bone fracture treating devices comprising external fixators, wherein pins are adapted to be extended through the skin and soft tissue of the patient into the bone in both upstream and downstream locations relative to the fracture site, are at times quite heavy in their constructions and may cause a compression in the fracture site, while, upon occasion, not being able to rigidly clamp together the fractured bone sections in an appropriately aligned and immobilized manner which would propagate the rapid healing thereof. That represents a problem, which in particular is encountered in fractures of the distal radius of the forearm of a patient, in that only a minimal amount of space is available for setting the fractured bone segments in a manner without adversely affecting the mobility of the patient's hand and fingers, while concurrently ensuring the provision of a lightweight structure, which is conducive towards affording a high degree of comfort to the patient during the normally prolonged period of healing necessary for the correction and treatment of such fractures, especially those which are encountered by young and tender patients, such as children and adolescents.

2. Discussion of the Prior Art

Thus, Faccioli, et al., U.S. Pat. No. 5,728,096, discloses an external trochanter splint in which a plurality of pins are adapted to extend into the bone of the patient at the upstream and downstream locations of the fracture. However, this particular structure is primarily designed to provide mobility to the knee of a patient and is of an extremely complicated and heavy arrangement in an attempt of ensuring mobility of the knee. The splint device would not be particularly suitable for providing fixing of the fracture at the distal radius of a forearm of a patient, due to its heavy weight and bulky complexity, while avoiding immobilizing the hand of the patients, which also considerably enhances or increases the costs thereof, and raises the risk of Ligamentotaxis.

Faccioli, et al, U.S. Pat. No. 5,951,556, discloses a compact external fixation device, wherein pins extending from a swivable external clamping unit are adapted to extend into the forearm bone of the patient downstream of a fracture, and further pins are adapted to extend into the bones of the patient's hand. Although, this fixation device is particularly intended to be generally employed for treating bone fractures of children; as can be ascertained, in this instance the complexity of the device of this patent and the weight thereof is such as to render it rather cumbersome and expensive, while adding to the discomfort of the patient, particularly a young child who may be unwilling or unable to support the weight of such a fixation device in a comfortable manner over a protracted period of time, as may be required for the fracture healing process.

Day, U.S. Pat. No. 4,135,505, also discloses a device utilizing pins or screws mounted on a splint-like bar, which pins are adapted to be introduced into the bone of a patient both upstream and downstream of a fracture site, and which includes adjustable means for maintaining the fracture in a correct treatable position. This is a relatively complex orthopedic fixation apparatus, which may not be able to be readily employed in a restricted spatial area, such as that containing the fracture site in a distal radial portion of a forearm, particularly that of a child or infant.

Similarly, Mraz, U.S. Pat. No. 2,333,033, includes a structure for orienting bone fixing pins in angular positions upstream and downstream pins of a fracture site, wherein the pins are mounted on a bar comprising a complicated gear mechanism for adjusting and fixing the axial positioning of the bone segments on the opposite sides of the fracture. This results in a heavy and cumbersome structure, which cannot be easily employed in the fixation of bone segments which are subjected to a distal radial fracture in the forearm of a patient.

The foregoing is also applicable to Siebrandt, U.S. Pat. No. 2,435,850, which includes a plurality of screws extending from a splint, and which are anchored in the bone of a patient on opposite locations of a fracture site, and which also would not be practical or applicable to the correction of a fracture in the distal radius of a forearm of a patient, while maintaining the mobility of the patient's hand.

Similarly, Goudfrooy, U.S. Pat. No. 4,299,212 discloses an external fracture immobilization splint having a plurality of mutually angled and intersecting pins adapted to be inserted into the bone of a patient, and with the pins being mounted on two axially movable heads located on the splint so as to be adjustably located on the upstream and downstream sides of a fracture site. This is a relatively complicated and heavy structure which is adapted to provide for sliding adjustable movement along a rod of the splint, and is not readily applicable for use in the setting of fractures in the distal radius of a patient's forearm, in which a minimal amount of space and weight is required in the stabilization of open and/or unstable fractures of the distal radius.

Agee, et al., U.S. Pat. No. 4,922,896, also discloses a colles' fracture split, which is adapted to employ pins extending into the bone on one side of a bone fracture and a pivotal element mounted on a bar for insertion into the bone of a patient on the opposite side, wherein a metacarpal bar can be rotated about an axis parallel to the longitudinal axis of the element, so as to provide limited motion to the hand of a patient.

Other patents of varying degrees of interest, which are directed to the treatment of bone fractures, are Helland, U.S. Pat. No. 4,488,542; Evans, et al., U.S. Pat. No. 4,271,832; and Weisenbach, U.S. Pat. No. 1,789,060.

Although all of these foregoing and numerous other orthopaedic external fixation devices are adapted to provide for the immobilization and healing correction of fractures in patient's bones, none of these are capable of providing a lightweight external wrist fixator device in accordance with the present invention.

SUMMARY OF THE INVENTION

In connection with providing an improvement with respect to the foregoing, state of the art, pursuant to the present invention, for the treatment of a fracture site, there is provided a cross-pin equipped external wrist fixator which is intended to ensure the absence of any Ligamentotaxis, wherein the external wrist fixator comprises a pair of slidably interconnected bar sections forming an axially adaptable external splint, with predetermined angled holes adapted to receive standard bone fixation wires at specified angular orientations for fracture fixation. In essence, a plurality of the crossed or intersecting wires are mounted on a distal section of the bar and a further plurality of crossed or intersecting pins on the proximal section of the external fixator slide bar sections, wherein the latter are axially adjustable and locked into fixed engagement by suitable locking means.

In essence, the above-mentioned angled and mutually crossing plurality of pins which extend through the bone of the patient in the region of the fractured distal radius, so as to mutually cross each other so as to traverse the fracture site, enables the stabilization of an open and/or unstable fracture of the distal radius of the forearm, in which a possible soft tissue injury may preclude the use of alternative fracture management devices and methods, such as pinning, casting or other types of external fracture fixation. Basically, the inventive external wrist fixation device, which facilitates the fixation of the distal radius fracture of a patient's forearm, without the crossing or extending over the wrist joint, which could result in immobilizing the wrist, thus avoids Ligamentotaxis and enables the fixing of the fractured distal radius of the forearm in implementing a minimally invasive technique. The external fixation device is adapted to prevent any loss of reduction and settling of the fracture distal radius, as is presently and quite commonly encountered with the application of conventional techniques. Furthermore, the avoidance of the Ligamentotaxis, the latter of which is a result of the pinning of the fingers of the patient, will eliminate the traumatizing of the wrist joint and facilitate an early mobilization of the wrist, elbow and forearm motion, thereby reducing the time period needed for the rehabilitation of the fracture.

To that extent, the lightweight slide sections of a bar-shaped splint member which mount the plurality of the wires, which extend in specified angled intersecting and mutually crossing relationships with each other provides a unique cross-wire configuration at the radial head at which the wires cross through the distal radius bone fracture site, while being externally supported by the present bar-shaped splint of the axially adjustable external fixation device.

Accordingly, it is an object of the present invention to provide a unique orthopaedic external fixation device for the fixing and immobilizing of bone fractures.

Another object of the invention resides in the provision of an external wrist fixing device pursuant to the invention in which pins or wires which extend into and through the bone of the patient at the fracture site traverse the latter, and are at unique angular intersecting relationships to each other, so as to have their essentially crossing orientations within the fracture site ensure that the fractured bone segments on opposite sides of the fracture site are inhibited from rotation or movement relative to each other, and thereby enhance the rigid healing thereof in the absence of Ligamentotaxis being encountered by the patient.

Another object of the present invention is to provide a novel adjustable external wrist fixation device mounting a plurality of mutually crossing or intersecting pins, which are adapted to extend through the bone of a patient so as to traverse the fracture site, such as that encountered at the distal radius of a forearm, and wherein the external fixation device is of minimal weight, of a compact and inexpensive structure, while imparting a maximum degree of comfort to a patient during the prolonged period of use thereof required for the treatment and healing of the fracture.

BRIEF DESCRIPTION OF THE DRAWINGS

Reference may now be made to the following detailed description of a preferred embodiment of the invention, taken in conjunction with the accompanying drawings; in which.

Figure 1:
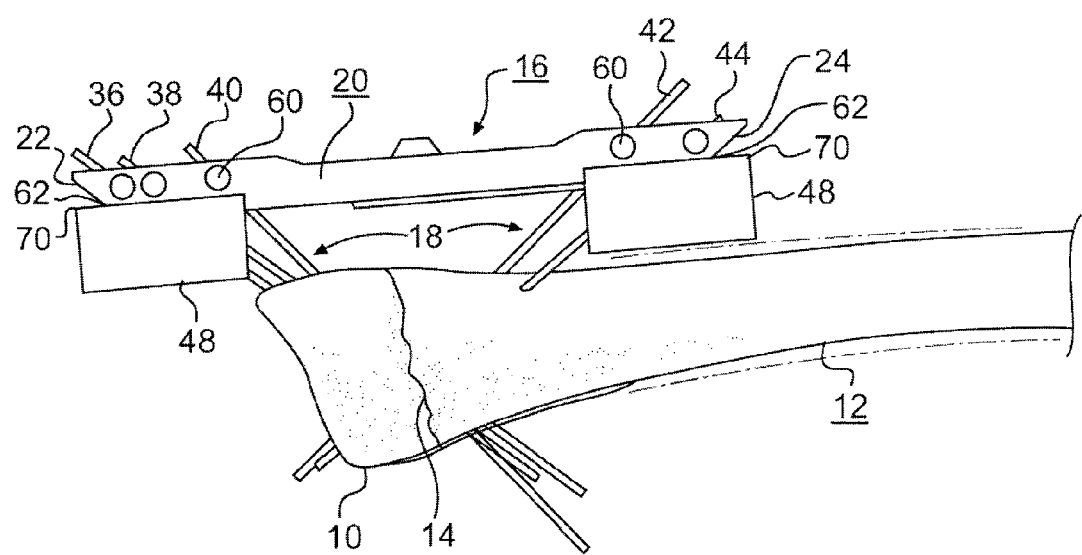
FIG. 1 illustrates a generally diagrammatic illustration of the inventive external fixation device for bone fractures with positioning spacers as applied to a fracture of the distal radial portion of the forearm of a patient.

Referring in detail to FIG. 1 of the drawings, there is illustrated the distal radius portion 10 of the forearm 12 of a patient showing a fracture site 14, which extends through the distal radius portion of the forearm proximate the wrist. In order to impart an immobilization to the fracture site 14, there is provided the inventive external fixation device 16, which, in this instance, employs a novel cross-pin arrangement 18 for fracture fixation without having to immobilize the wrist portion of the patient, thereby avoiding the effects of Ligamentotaxis, which could unduly cause a high degree of discomfort to the patient and also necessitate a lengthy period of rehabilitation in order to again attain full mobility of the wrist joint at the injured site.

In particular, as described in further detail hereinbelow, the basically orthopaedic wrist external fixation device 16 includes an axially adjustable bar or splint structure 20, generally rectangular in transverse cross-section which may be constituted of a lightweight material, such as titanium and comprised of slidably interengagable and mutually lockable distal and proximal elongate base portions 22, 24, which are adjusted relative to each other in correlation with the size of the forearm 12 of the patient, and the specific location of the distal radius fracture to which the forearm has been subjected. Each of the bar portions 22, 24 includes a plurality of angularly extending through holes 26, 28, 30, 32, 34 oriented from the top to the bottom of the bar portions, as described more specifically hereinbelow. Hereby, the holes 26, 28, 30 in the distal base portion 22 are angled in a direction towards the proximal portion 24, whereas the holes 32, 34, which are formed in the proximal base portion 24 of the bar 20 of the external fixation device 16 are angled so as to slope or incline towards the distal base portion 22 of the fixation device 16. Consequently, upon the insertion of bone fracture-setting wires or pins 36, 38, 40, 42, 44 through the holes in the respective proximal and distal bar portions of the bar structure 20 or splint, and the extension of the pins through the fracture site 14, the pins which may be standard Kirschner Wires (K-wires), preferably formed of surgical grade steel, as shown more clearly in FIG. 3 of the drawings, intersect or cross each other so as to form a rigid lattice-type or framework pin arrangement within the fracture site, which will traverse and retain the fractured bone portions of the forearm on opposite sides of the fracture site 14 in a fixed and correctly aligned contacting manner, secured against mutual rotation, so as to propagate the rapid healing thereof at a minimum degree of discomfort to the patient. An appropriate spacing of the bar structure or splint 20 of the external fixation device 16, with regard to contacting the skin or surface of the forearm, is ensured by detachable positioning spacers 48, which are mounted at the spaced apart ends of the distal and proximal bar portions 22, 24 during the locating deployment of the external fixation device 16.

Figure 2:
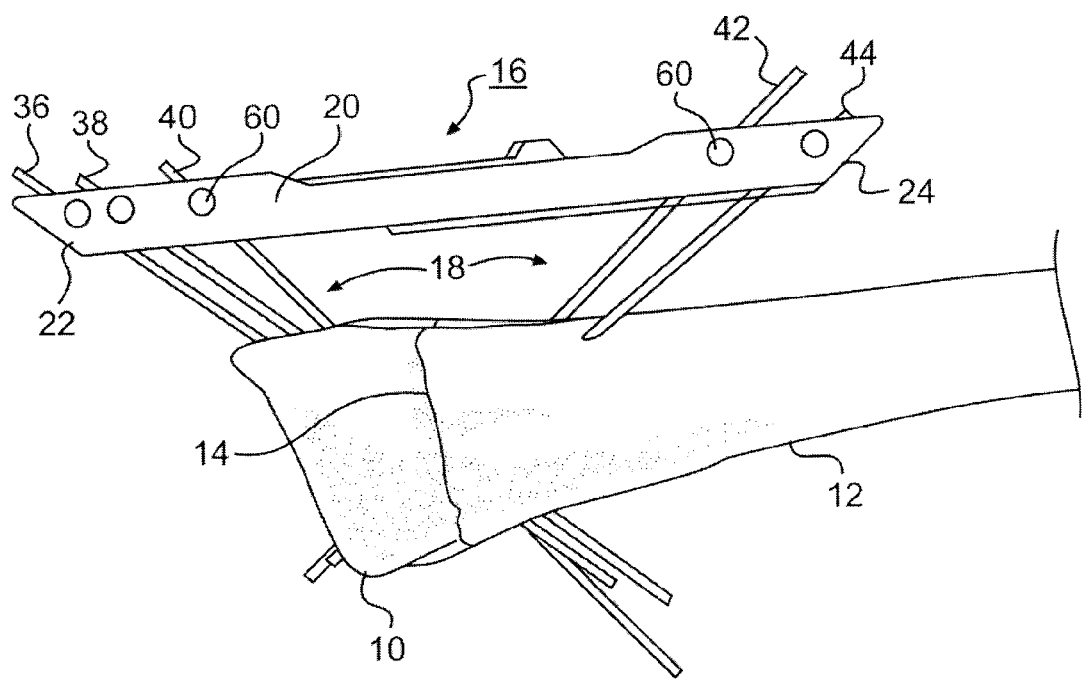
FIG. 2 illustrates the external fixation device for bone fractures as attached to the forearm of a patient with the positioning spacers having been detached therefrom.

As shown in FIG. 2 of the drawings, upon completing the appropriate positioning of the external fixation device 16 and the arrangement 18 of the pins which are mounted in the holes of the splint 20 and which extend through the bone fracture site 14, upon the locking of the pins in the holes of the device, the positioning spacers 48 which are mounted at the opposite ends of the fixation device in a slidable engagement therewith, are removed by simple sliding off mating guideways or slots formed in the sides of the bar portions 22, 24, as described hereinbelow, and thereafter the external arm area about the entire fracture site may be suitably bandaged, as is well known in the medical technology.

Figure 3:
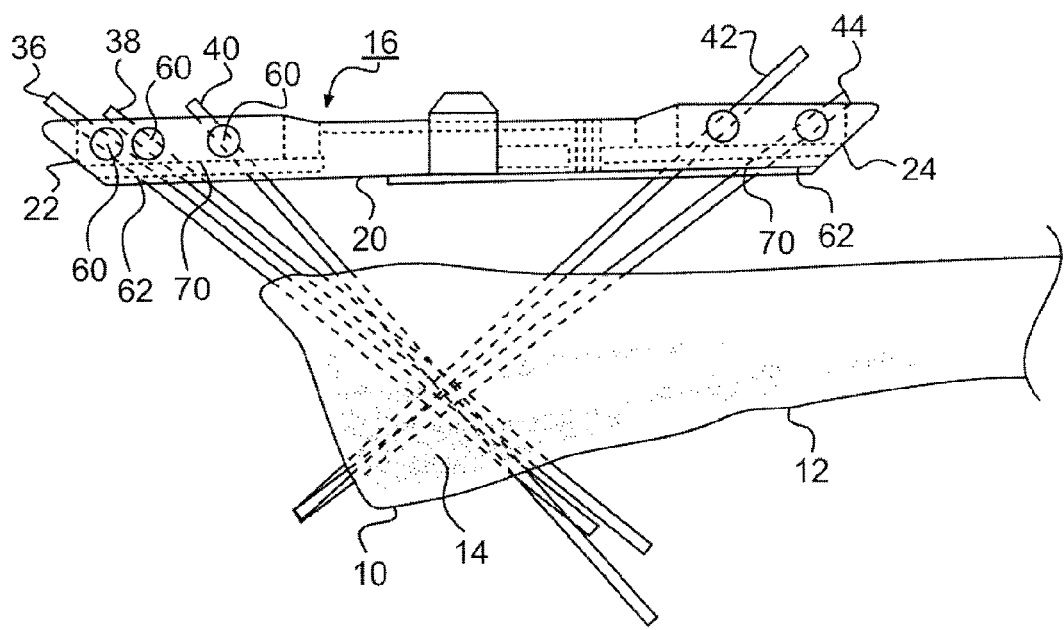
FIG. 3 illustrates a computerized schematic representation showing the external fixation device as attached to the fractured distal radial portion of the forearm and illustrating the positioning of the fracture setting and immobilizing pins relative to the fracture site.
Figure 4:
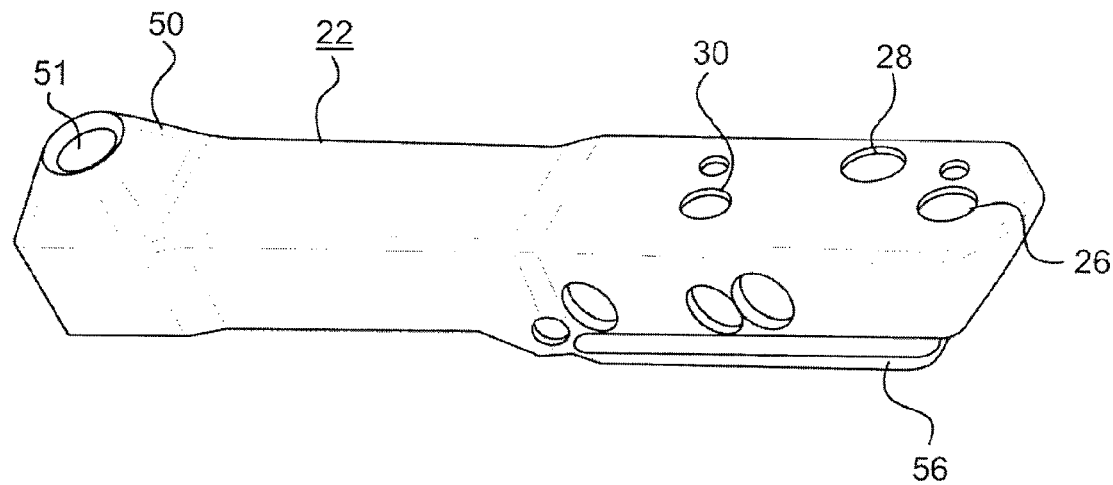
FIG. 4 illustrates, in a top and side perspective view, a distal base portion of the external fixation device.
Figure 5:
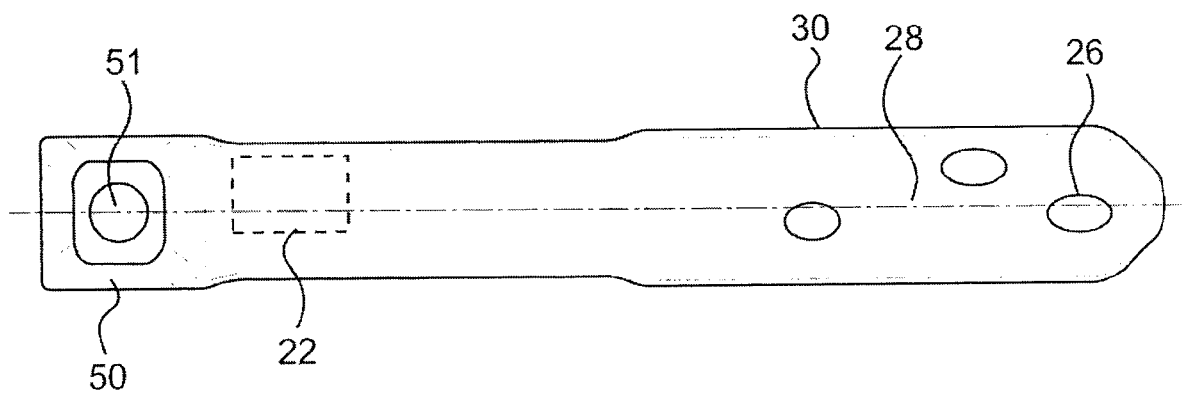
FIG. 5 illustrates a top plan view of the distal base portion.
Figure 6:
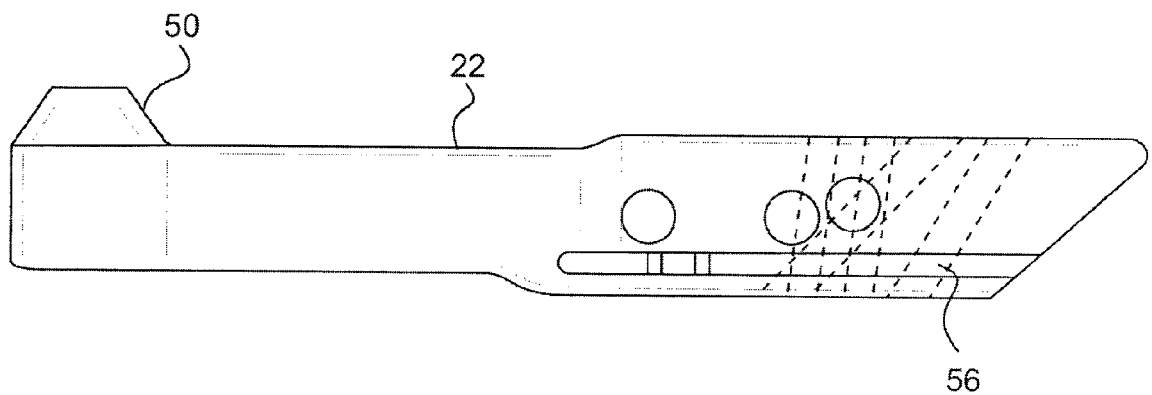
FIG. 6 illustrates a side view of the distal base portion of the external fixation device.
Figure 7:
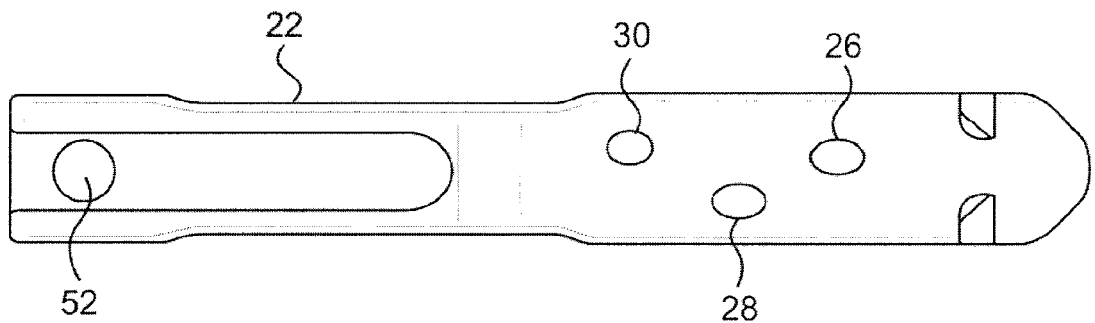
FIG. 7 illustrates a bottom plan view of the distal base portion.
Figure 8:
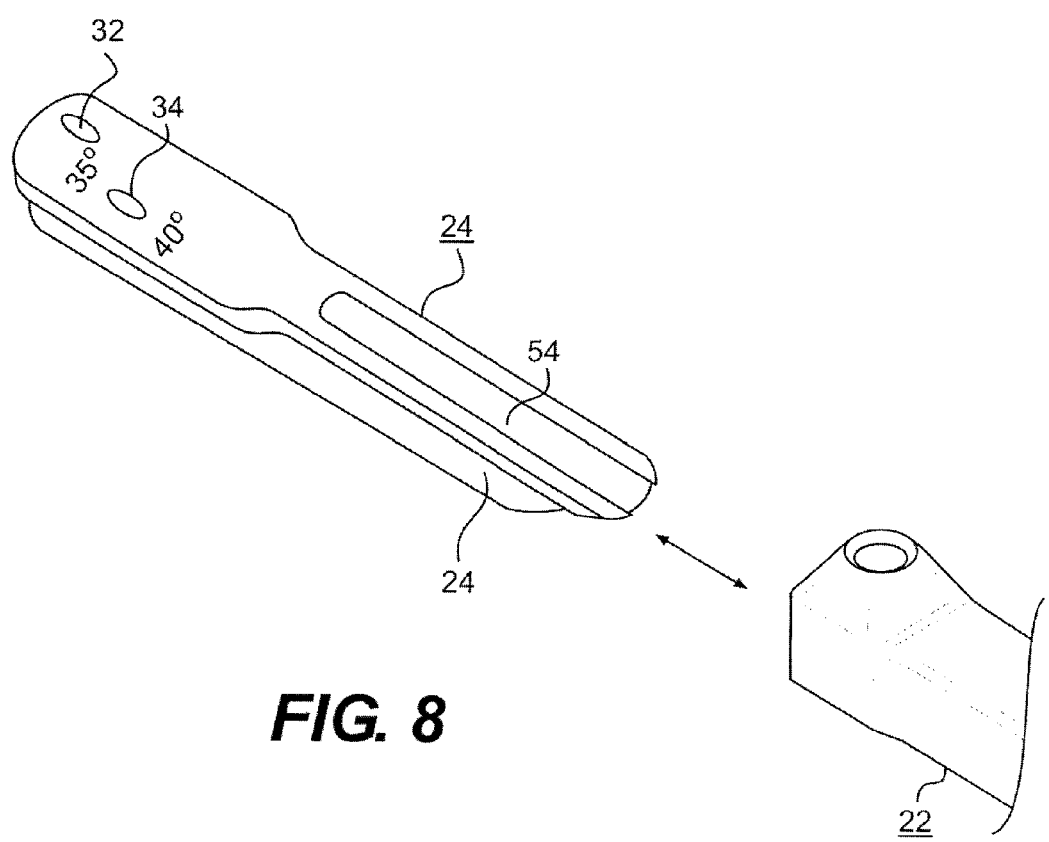
FIG. 8 illustrates a side and perspective view of the proximal base portion of the external fixation device, which is adapted to be adaptably and slidably interconnected with the distal base portion.
Figure 9:
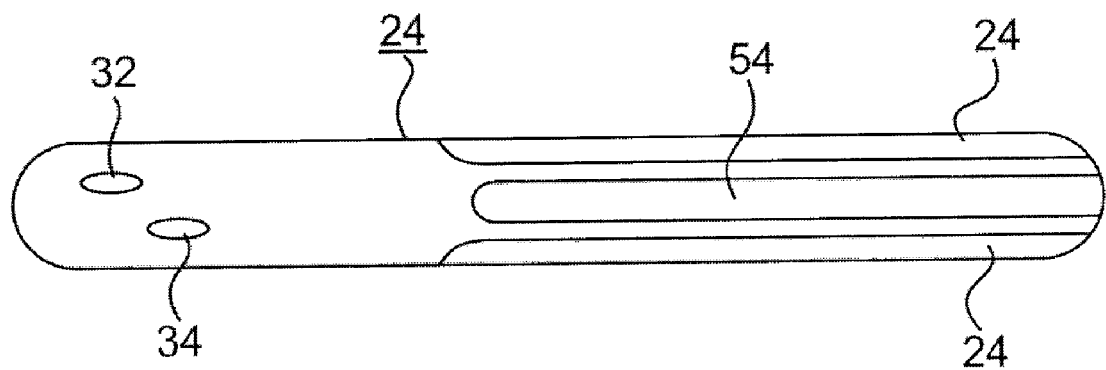
FIG. 9 illustrates a top plan view of the proximate external fixation device base portion.
Figure 10:
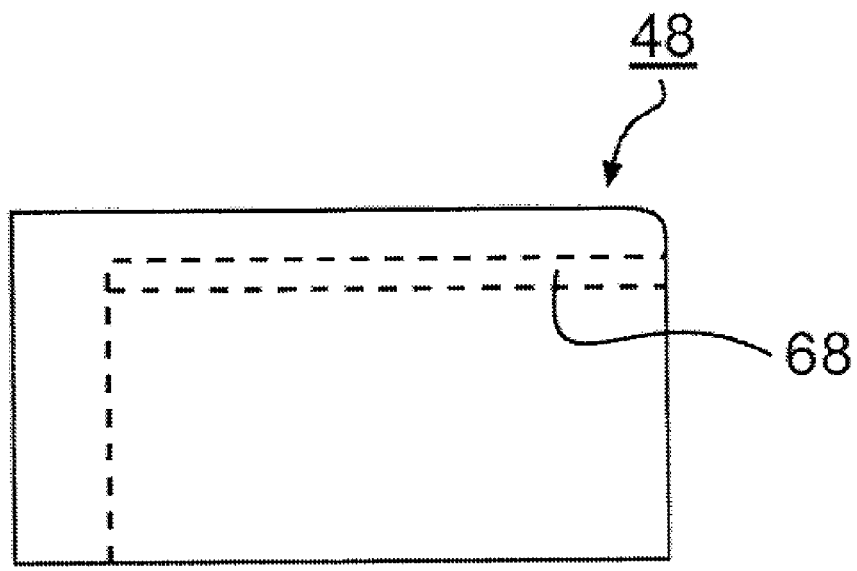
FIGS. 10-13 illustrate, respectively, top, side, bottom and end views of a positioning spacer for developing the external fixation device, as shown in FIG. 1 of the drawings, on the forearm of a patient proximate the fracture site.
Figure 11:
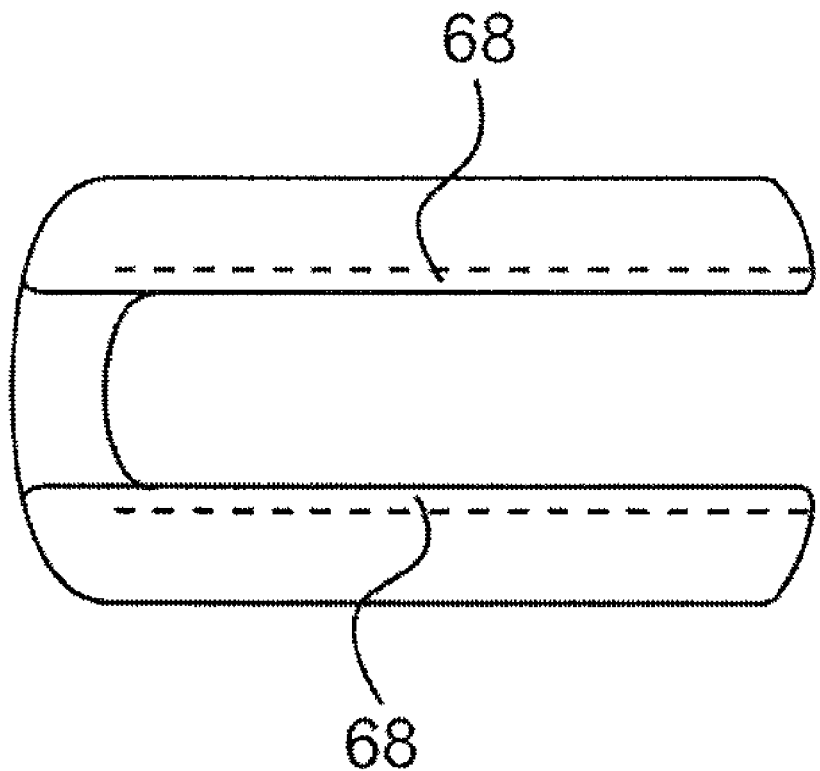
Figure 12:
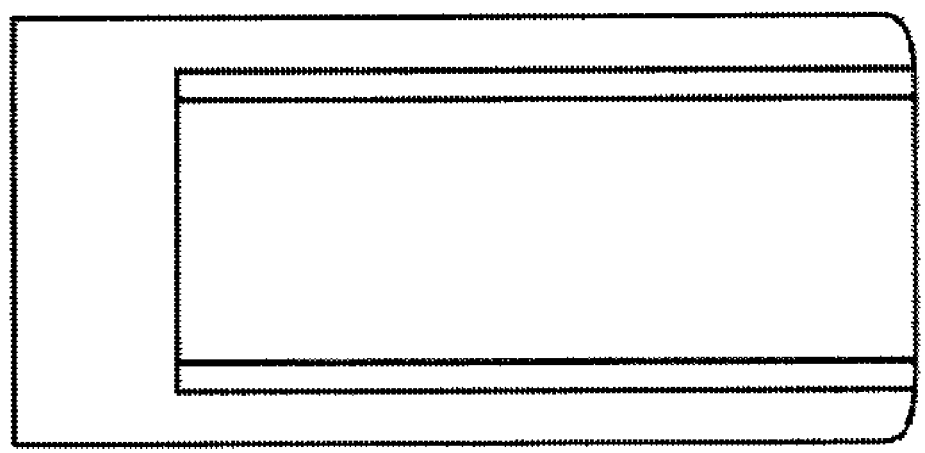
Figure 13:
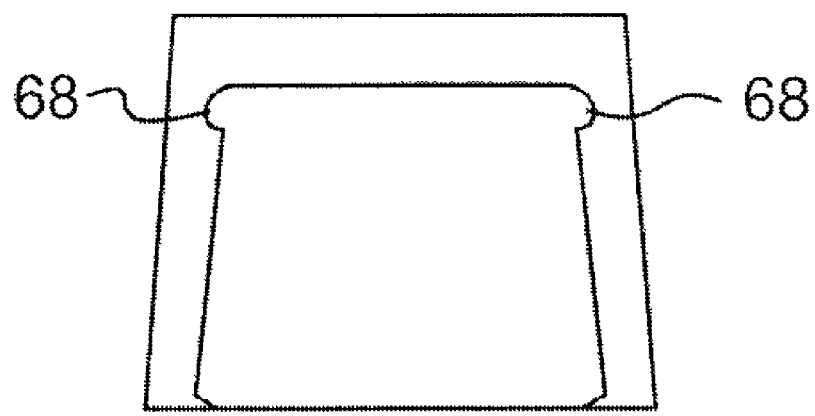

Reverting in more specific detail to the inventive external fixation device 16, as shown in FIGS. 4-9, having particular reference to the distal external fixator base portion 22 of the splint 20, there are provided a plurality of the angled holes 26, 28, 30; in this instance, three (3) holes extending downwardly therethrough at angles of within a range of 30° to 60° from the vertical, depending upon the fracture site and patient size, these holes being adapted to receive the bone-setting pins, which are to be passed through the bone at the fracture site. The holes 26, 28, 30 are each differently angled so as to pass through the fracture site 14 at intersecting or crossing relationships, as shown in FIG. 3 of the drawings. The holes 26, 28, 30 are angled so as to be directed downwardly towards pins 30, 34, which are angled in the opposite inward orientation from the proximal base portion 24 so as to intersect the pins 26, 38, 30 when extending through the bone in the fracture site 14. These pins 32, 34 also subtend angles within the range of 25° to 60° from the vertical, and form an intersecting cross-over pattern with each other and the remaining pins upon insertion through the fracture site 14. Preferably, although not necessarily, the pins subtend angles with the vertical (normal) by pin 26 of about 40°; pin 28 of about 41°; and pin 30 of about 50°. The pins 32, 34, which are angled towards pins 26, 28, 30, subtend angles with the vertical by pin 32 of about 35° and pin 34 of about 40°. All of the foregoing angles are exemplary only, and the fixation device may have pin holes formed therethrough at various other orientations. Moreover, the number of pins can also be modified in accordance with other external fixation devices, as required.

The illustrated distal external fixator base portion 22 is an elongated bar member having a raised portion 50 on an upper surface containing a screw-threaded aperture 51 for receiving a set screw 52 adapted to engage in a recessed grooved surface 54 of the proximal bar portion 24 and to be able to be locked thereto by means thereof when the base portion 22, 24 are in slidable engagement through cooperating opposite side grooves 54 on the base portion 24 and therewith contacting lips 56 on the base portion 22.

The elongated base portions 22, 24 also include transverse side apertures 60 for elements (not shown) for locking the pins into position in the base portions upon the insertion of the pins into the bone of the patient, so as to prevent the fixation device splint 20 from being moved along the pins, or conversely the pins being axially displaced within the holes which are provided therefor in the splint.

The lower end portion of each base portion 22, 24 may be provided with side slots 62 extending along partially the length of each lower side edge so as to enable positioning spacers 48 to be slid thereon in order to facilitate positioning of the external fixation device on the forearm of the patient proximate the fracture site, and to be thereafter easily removed by being pulled off when the device is in its final deployed position.

With regard to the positioning spacers 48, these are essentially U-shaped members, which are adapted to have slits 68 provided on opposite internal sides so as to engage over projections 70 below the slots 62 provided in the lower edges of the proximal and distal fixation base portions 22, 24 and which enable these spacers, which may be constituted of a suitable plastic material, to be easily removed when the positioning of the fixation device 16 with regard to the fracture site 14 is completed.

The external fixation device 16 itself, in effect, the base portions 22, 24 of the distal and proximal segments of the splint, may be constituted of lightweight titanium, and the pins or wires may also be suitably constituted of surgical steel or similar medically-compatible materials, as is known in the technology, such as Kirschner Wires.

In summation, as previously set forth hereinabove, the invention facilitates the stabilization of open and/or unstable fractures of the distal radius, where soft tissue injury may preclude the use of alternative fracture management such as pinning, casting, and any other type of external fixation. External fixation of the fractured distal radius without crossing over the wrist joint and avoiding Ligamentotaxis is desired, and to fix a fractured distal radius with a minimally invasive technique. Preventing loss of reduction and settling of the fractured distal radius is commonly encountered with conventional techniques, whereas avoiding Ligamentotaxis to achieve and maintain reduction; will result in sparing the wrist joint. Early mobilization of the wrist, elbow and forearm motion, minimizing rehabilitation of the fracture, are achieved by the present invention.

From the foregoing, it becomes readily apparent that there is provided a general universal type of orthopaedic external wrist fixation device, which due to its simplicity of construction and lightweight, is particularly suitable for use with young patients, such as adolescents or children, and provides a minimum degree of discomfort and a short healing time for the fracture.

While there has been shown and described what is considered to a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. An external fixation device for the setting and corrective treatment of bone fractures, comprising:
    a splint member positionable externally of the site of the fracture, said splint member having first and second axially slidable and mutually fastenable base portions for adjusting the length of said splint member;
    each of said base portions of said splint member mounting a set of bone pins, wherein said bone pins in each base portion extending at mutually converging angles with respect to each other and with respect to said bone pins in the other base portion from said respective base portions for traversing the site of the bone fracture, and forming a mutually crossing and intersecting pin arrangement at the site of the bone fracture so as to fix any fractured bone segments at said bone fracture site in position secured against rotation and axial movement,
    wherein said first and second base portions of said splint member are each elongated bars which are axially slidably interconnected so as to extend along a common axis; and fastening structure being provided on one of said base portions for locking said other base portion thereto in predetermined axially adjusted positions,
    wherein said splint member has axially extending grooves and cooperating lips formed extending along at least a portion of the lengths of each of said base portions to facilitate adjustment of the axial length of said splint member and resulting spacing between the sets of pins between said base portions,
    wherein positioning spacers are detachably mounted on the outer ends of said base portions to facilitate the radial spacing of said device relative to the location of the bone fracture site during the deployment of the splint member for fixation of the fracture site, and
    wherein said positioning spacers are arranged so as to be mounted on grooves formed in the lower side edges of each said base portion, and are axially slidably detachable upon completion of the deployment of said splint member proximate said fracture site.

2. An external fixation device, as claimed in claim 1, wherein said sets of pins of each of said first and second base portions of said splint member cross through said fracture site and mutually intersect so as to form a lattice arrangement extending through and immobilizing said bone fracture site.

3. An external fixation device, as claimed in claim 1, wherein said first base portion of said splint comprises a proximal base segment and said second base portion of said splint comprises a distal base segment, wherein each set of said bone pins includes a specified number of bone pins.

4. An external fixation device, as claimed in claim 3, wherein said proximal base segment mounts at least two of said bone pins and said distal base segment mounts at least two of said bone pins.

5. An external fixation device, as claimed in claim 4, wherein said two bone pins in said proximal base segment subtend angles relative to the normal extending through said splint member and into said fracture site within a range of about 25° to 60°.

6. An external fixation device, as claimed in claim 5, wherein a first bone pin of said two bones pins located towards an outer end of said proximal base segment subtends an angle about 35° and a second bone pin of said two bone pins located axially inwardly subtends an angle of about 40° relative to a normal.

7. An external fixation device, as claimed in claim 4, wherein said three bone pins in said distal base segment subtend angles relative to the normal extending through said splint member and into said fracture site within a range of about 30° to 60°.

8. An external fixation device, as claimed in claim 7, wherein a first bone pin of said three bone pins located towards an outer end of said distal base segment subtends an angle of about 40°, a second bone pin located axially inward thereof subtends an angle of about 41', and a third bone pin which is located furthermost axially inward subtends an angle of about 50° relative to a normal.

9. The external fixation device of claim 3, wherein said proximal base segment mounts at least three of said bone pins and said distal base segment mounts at least three of said bone pins.

10. An external fixation device, as claimed in claim 1, wherein said fastening structure comprises at least one set screw for locking said base portions in predetermined axial adjustment relative to each other.

11. An external fixation device, as claimed in claim 1, wherein said base portions are each rectangular in transverse cross-section so as to inhibit relative rotational displacement between said base portions while enabling axial adjustment therebetween.

12. An external fixation device, as claimed in claim 1, wherein said splint member is constituted of a lightweight metallic material.

13. An external fixation device, as claimed in claim 12, wherein said metallic material comprises titanium.

14. An external fixation device, as claimed in claim 1, wherein said bone pins are each constituted of a surgical-grade metal.

15. An external fixation device, as claimed in claim 14, wherein said surgical-grade metal comprises surgical steel.

16. An external fixation device, as claimed in claim 1, wherein said bone pins comprise standard Kirschner wires (K-wires).

* * * * *